US010659861B2

(12) United States Patent
England et al.

(10) Patent No.: US 10,659,861 B2
(45) **Date of Patent: *May 19, 2020**

(54) COMPOSITE EARCUSHION

(71) Applicant: BOSE CORPORATION, Framingham, MA (US)

(72) Inventors: Raymond O. England, East Greenich, RI (US); David Meeker, Acton, MA (US); Richard L. House, Hartford, ME (US); Derek J. Stacey, Auburn, ME (US)

(73) Assignee: BOSE CORPORATION, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/250,273

(22) Filed: Jan. 17, 2019

(65) Prior Publication Data

US 2019/0149904 A1 May 16, 2019

Related U.S. Application Data

(63) Continuation of application No. 15/716,796, filed on Sep. 27, 2017, now Pat. No. 10,187,716.

(51) Int. Cl.
*H04R 25/00* (2006.01)
*H04R 1/10* (2006.01)
(Continued)

(52) U.S. Cl.
CPC ......... *H04R 1/1008* (2013.01); *H04R 1/1058* (2013.01); *H04R 1/1083* (2013.01);
(Continued)

(58) Field of Classification Search
CPC .......... G10K 2210/1081; H04R 1/1008; H04R 1/1058; H04R 1/1083; H04R 1/288; H04R 5/033
(Continued)

(56) References Cited

U.S. PATENT DOCUMENTS 3,691,565 A * 9/1972 Galonek .................. A61F 9/02 2/431
4,989,271 A * 2/1991 Sapiejewski ............ A61F 11/14 2/209

(Continued)

FOREIGN PATENT DOCUMENTS

| | | | |
|---|---|---|---|
| CN | 206402413 | U | 8/2017 |
| EP | 2248350 | B1 | 7/2015 |
| WO | 201517484 | A2 | 2/2015 |

OTHER PUBLICATIONS

International Search Report and Written Opinion from corresponding International Application No. PCT/US2018/052608 dated Nov. 29, 2018.

*Primary Examiner* — Khai N. Nguyen
(74) *Attorney, Agent, or Firm* — Lando & Anastasi, LLP

(57) ABSTRACT

An earphone cushion includes a body formed of a partially reticulated polymeric foam and including a front surface configured to engage or surround the ear of a user, and a rear surface, a snap ring at least partially embedded in and integrally formed with the body and including a periphery configured to engage one or more retention elements of an earcup of a headphone, and a non-porous film on the front surface of the body.

26 Claims, 13 Drawing Sheets

(51) Int. Cl.
*H04R 1/28* (2006.01)
*H04R 5/033* (2006.01)

(52) U.S. Cl.
CPC ............. *H04R 1/288* (2013.01); *H04R 5/033* (2013.01); *G10K 2210/1081* (2013.01)

(58) Field of Classification Search
USPC .......................................................... 381/371
See application file for complete search history.

(56) References Cited

U.S. PATENT DOCUMENTS

| | | | | | |
|---|---|---|---|---|---|
| 5,328,244 | A * | 7/1994 | Ishihara | B60N 2/882 | 297/391 |
| 5,590,213 | A * | 12/1996 | Urella | H04R 5/0335 | 381/370 |
| 5,911,314 | A * | 6/1999 | Urella | A61F 11/14 | 2/209 |
| 6,229,901 | B1 * | 5/2001 | Mickelson | A61F 11/008 | 181/128 |
| 6,295,366 | B1 * | 9/2001 | Haller | H04R 5/0335 | 379/430 |
| 6,466,681 | B1 * | 10/2002 | Siska, Jr. | H04R 5/0335 | 381/370 |
| 6,597,792 | B1 * | 7/2003 | Sapiejewski | H04R 1/1083 | 381/371 |
| 6,856,690 | B1 * | 2/2005 | Skulley | H04R 1/1008 | 381/367 |
| 6,940,007 | B2 * | 9/2005 | Schmidt | G10D 9/043 | 84/385 P |
| 7,162,039 | B1 * | 1/2007 | Callahan | A61B 7/02 | 381/374 |
| 8,098,872 | B2 * | 1/2012 | Chang | H04R 1/1075 | 381/370 |
| 8,170,262 | B1 * | 5/2012 | Liu | H04R 1/1016 | 381/382 |
| 8,467,539 | B2 | 6/2013 | Sapiejewski et al. | | |
| 8,699,740 | B2 * | 4/2014 | Chiang | H04R 1/1075 | 29/594 |
| 9,823,737 | B2 * | 11/2017 | Mazed | G06F 3/011 | |
| 9,902,127 | B2 * | 2/2018 | Peskar | A61F 11/14 | |
| 10,187,716 | B1 * | 1/2019 | England | H04R 1/1008 | |
| 2008/0069391 | A1 * | 3/2008 | Steyn | H04R 1/1025 | 381/371 |
| 2008/0187151 | A1 * | 8/2008 | McClenon | H04R 1/12 | 381/74 |
| 2008/0226111 | A1 * | 9/2008 | Wang | H04R 1/1058 | 381/375 |
| 2010/0119076 | A1 * | 5/2010 | Monk | A61F 11/14 | 381/71.6 |
| 2010/0124653 | A1 * | 5/2010 | Tadros | B32B 3/30 | 428/316.6 |
| 2011/0007928 | A1 * | 1/2011 | Chang | H04R 1/1075 | 381/378 |
| 2011/0031059 | A1 * | 2/2011 | Parish | A61F 11/08 | 181/129 |
| 2013/0022225 | A1 * | 1/2013 | Chiang | H04R 1/1008 | 381/371 |
| 2013/0087404 | A1 * | 4/2013 | Peskar | G10K 11/168 | 181/129 |
| 2014/0177898 | A1 * | 6/2014 | Granovetter | H04R 1/1016 | 381/380 |
| 2014/0211976 | A1 * | 7/2014 | Brunner | H04R 1/1066 | 381/374 |
| 2014/0302700 | A1 * | 10/2014 | Makinen | H01R 13/56 | 439/353 |
| 2014/0339014 | A1 * | 11/2014 | Varanasi | G10K 11/168 | 181/292 |
| 2015/0118932 | A1 * | 4/2015 | Buechler | C09D 5/00 | 442/370 |
| 2015/0307338 | A1 * | 10/2015 | Scott | B67B 3/2093 | 53/331.5 |
| 2016/0086458 | A1 * | 3/2016 | Biggs | G08B 6/00 | 381/151 |
| 2017/0006369 | A1 * | 1/2017 | Kenaley | B32B 5/02 | |
| 2017/0136733 | A1 * | 5/2017 | Peskar | A61F 11/14 | |
| 2017/0230746 | A1 * | 8/2017 | Silvestri | H04R 1/1083 | |
| 2018/0028099 | A1 * | 2/2018 | Shekarriz | A61B 5/14507 | |
| 2018/0041827 | A1 * | 2/2018 | Abdelmalek | H04R 1/1066 | |
| 2018/0070169 | A1 * | 3/2018 | Annunziato | H04R 1/1016 | |
| 2019/0149904 | A1 * | 5/2019 | England | H04R 1/1008 | |

* cited by examiner

COMPOSITE EARCUSHION

CROSS-REFERENCE TO RELATED APPLICATIONS

This application claims priority under 35 U.S.C. § 120 as a continuation of U.S. patent application Ser. No. 15/716,796, titled COMPOSITE EARCUSHION, filed Sep. 27, 2017, now U.S. Pat. No. 10,187,716, which is incorporated by reference herein in its entirety for all purposes.

TECHNICAL FIELD

Aspects and implementations of the present disclosure are directed generally to a composite headphone earcushion and to headphones including same.

BACKGROUND

Wireless and mobile electronic devices are increasingly popular. In some instances, the sound generated by the wireless and mobile electronic devices is transmitted through wires to one or more speakers that are positioned adjacent to the user's ears. In some instances, the generated sound can be transmitted to speakers via wireless transmission devices. One example of a speaker system positioned adjacent to the user's ears is a set of headphones.

In addition to speakers, headphones can include materials for softening the contact of the headphones against the user's ear (a supra-aural design) or against portions of the user's head adjacent to the user's ears (a circum-aural design). The materials are intended to provide comfort to the user as the headphones are used and may reduce the amount of external noise reaching the user's ear and/or may absorb noise such as audio rendered by an audio driver of the headphones that is reflected from a portion of the user's ear or head, or any reverberant sound wave within the earcushion plenum These materials may be formed into what is referred to herein as earphone cushions or earcushions.

SUMMARY

In accordance with an aspect of the present disclosure, there is provided an earphone cushion. The earphone cushion comprises a body formed of a partially reticulated polymeric foam and including a front surface configured to engage or surround the ear of a user, side surfaces, and a rear surface, a snap ring at least partially embedded in and integrally formed with the body and including a periphery configured to engage one or more retention elements of an earcup of a headphone, and a non-porous film on the front surface and side surfaces of the body.

The rear surface of the body may be free of the non-porous film and may be substantially acoustically transparent.

The body may include a stepped portion extending from the rear surface of the body and onto one of an internal periphery and an external periphery of a rear surface of the snap ring. An outer peripheral portion of the rear surface of the snap ring may extend outwardly from beneath the stepped portion of the body.

An outermost periphery of a front surface of the snap ring may be coextensive with an outer periphery of the body.

Front and rear surfaces of the snap ring may be substantially planar.

The snap ring may include one or more rearwardly extending prongs configured to engage with one or more respective receptacles in the ear cup.

The snap ring may have a rigidity greater than a rigidity of the partially reticulated polymeric foam.

The earphone cushion may further comprise an acoustic dampener disposed within the body. The acoustic dampener may include a material having a density greater than a density of the partially reticulated polymeric foam. The acoustic dampener may be ring-shaped or oval-shaped.

An inner portion of the rear surface of the body may be substantially planar.

The rear portion of the body may include at least one cavity defined between an inner periphery and an outer periphery of the rear portion of the body.

An outer surface of the body extending forward from the snap ring may be free of creases and folded segments.

The partially reticulated polymeric foam may have a cell size of between about 100 μm and about 750 μm.

The non-porous film may include an acrylic material or any other thin film non-porous material having a composition different than the polymeric foam.

In accordance with an aspect of the present disclosure, there is provided a headset. The headset comprises an earcup having a front opening configured to be adjacent to an ear of a user when worn by the user and an earphone cushion sized to secure to the front opening of the earcup. The earphone cushion includes a body formed of a partially reticulated polymeric foam and including a front surface configured to engage or surround the ear of the user, and a rear surface, a snap ring at least partially embedded in and integrally formed with the body and including a periphery configured to engage one or more retention elements in the earcup, and a non-porous film integral with the front surface of the body.

The one or more retention elements in the earcup may include one or more detents extending inwardly from an inner wall of the earcup.

The snap ring may be configured to engage rear surfaces of the one or more detents to secure the earphone cushion to the front opening of the earcup.

The body of the earphone cushion may include a stepped portion extending from the rear surface of the body, onto an internal periphery of a rear surface of the snap ring, and into an interior portion of the earcup.

The one or more retention elements in the earcup may include one or more slots configured to receive one or more respective tabs extending from a rear surface of the snap ring.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
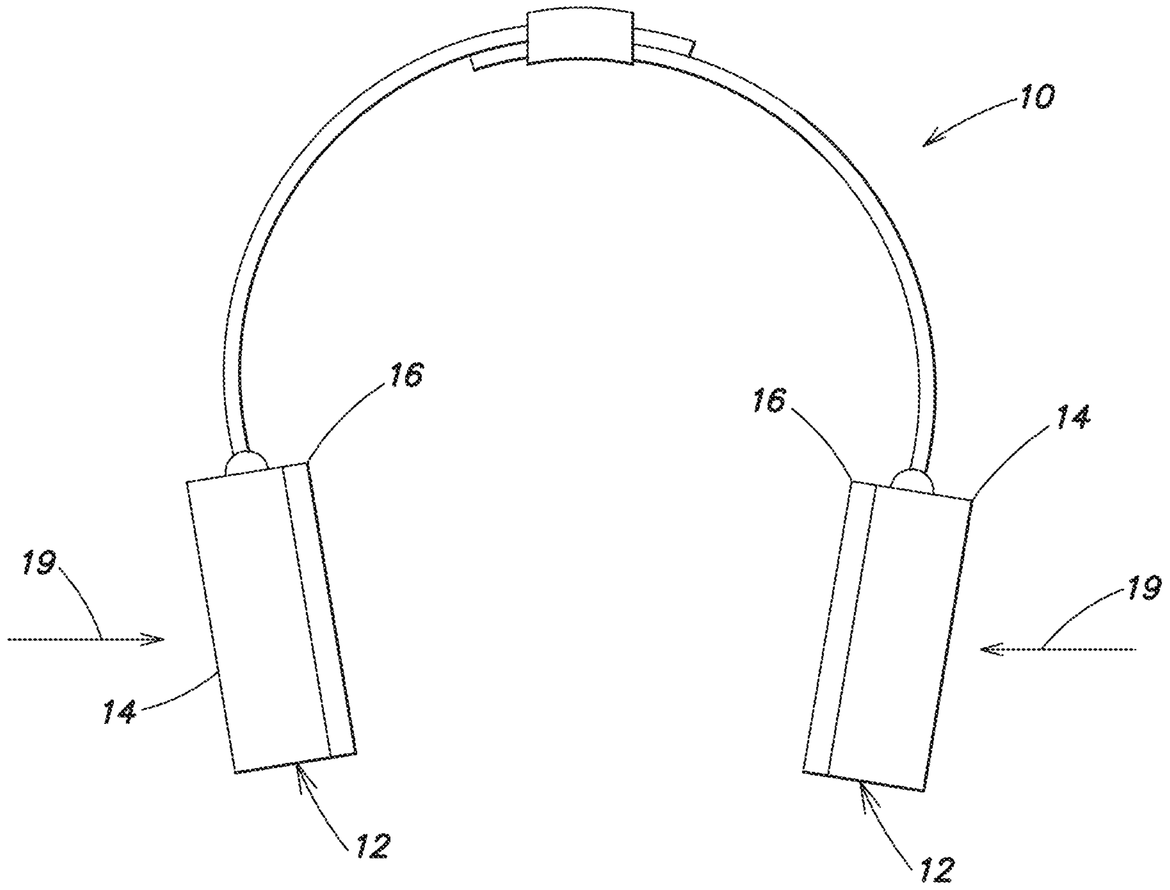
FIG. 1 is an elevation view of an example of a headphone.

Aspects and implementations disclosed herein are not limited to the details of construction and the arrangement of components set forth in the following description or illustrated in the drawings. Aspects and implementations disclosed herein are capable of being practiced or of being carried out in various ways.

Figure 2A:
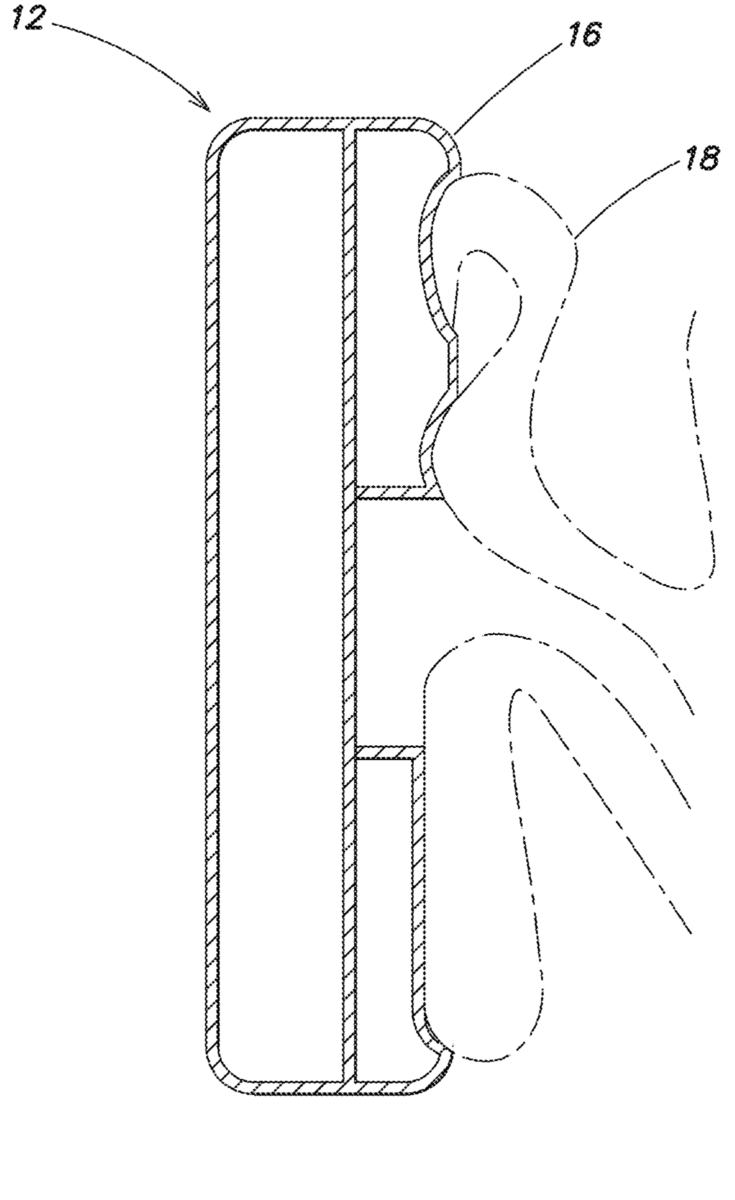
FIG. 2A illustrates an example of a supra-aural headphone earcushion disposed against an ear of a user.
Figure 2B:
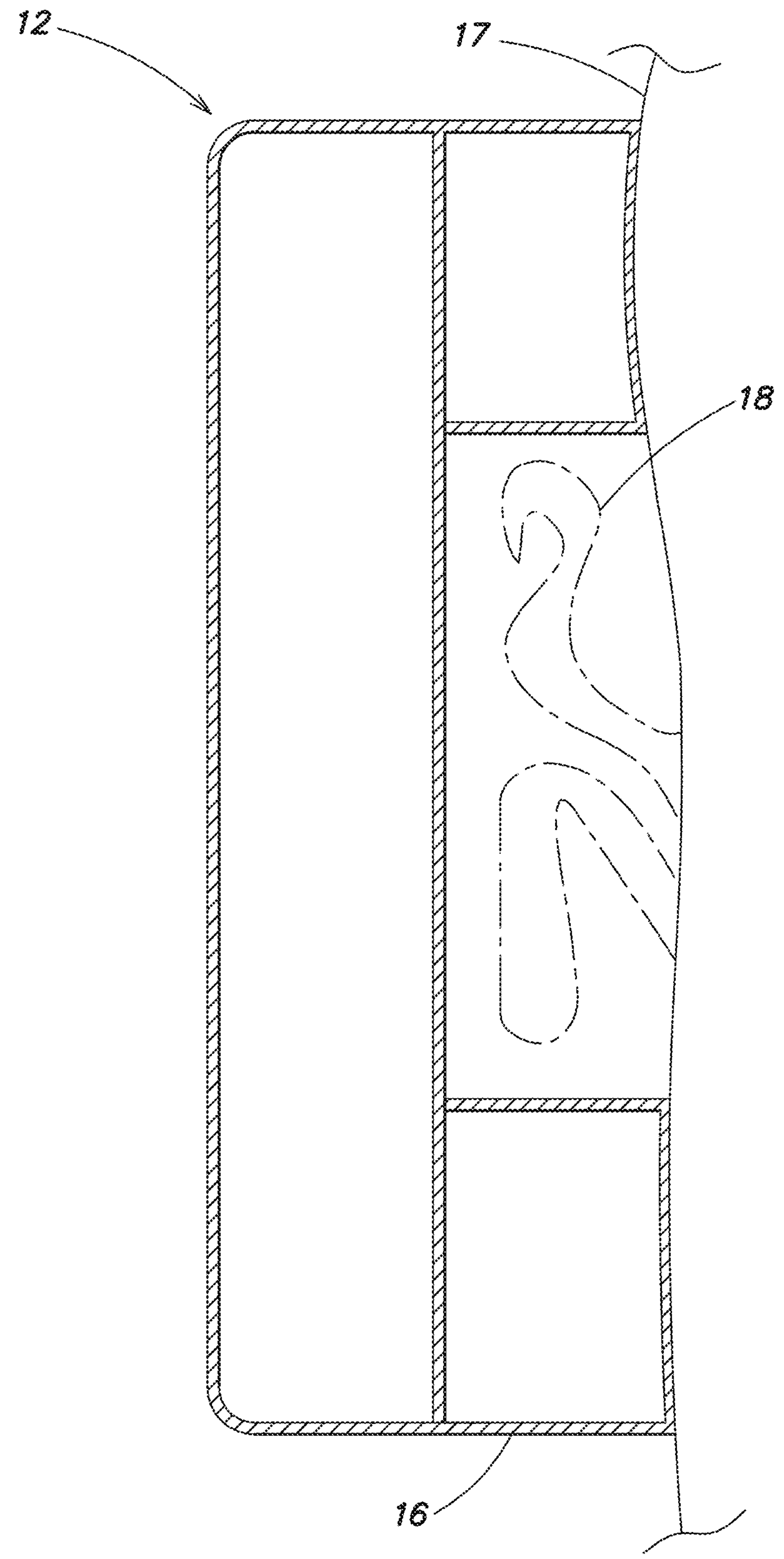
FIG. 2B illustrates an example of a circum-aural headphone earcushion disposed against a head of a user.

Referring to FIG. 1, there is shown an example of a headphone 10. The headphone 10 includes two earphones 12, connected by a headband. Each earphone 12 includes a cup shaped shell or earcup 14 and an earcushion 16. The headband exerts a force in an inward direction as represented by arrows 19. In some implementations, headphone 10 is a supra-aural headphone. When worn by a user, the earcushions 16 rest against the user's ears 18 and may deform slightly to form a seal against the user's ears 18, as illustrated in FIG. 2A. In other implementations, headphone 10 is a circum-aural headphone and when worn by a user, the earcushions 16 rest against portions of the user's head 17 surrounding the user's ears 18 and may deform slightly to form a seal against the portions of the user's head, as illustrated in FIG. 2B. The seal of the earcushion 16 against the ears of the user or against the portion of the head of the user about the ears of the user may reduce the total external acoustic energy reaching the ear canals of the user.

Figure 3A:
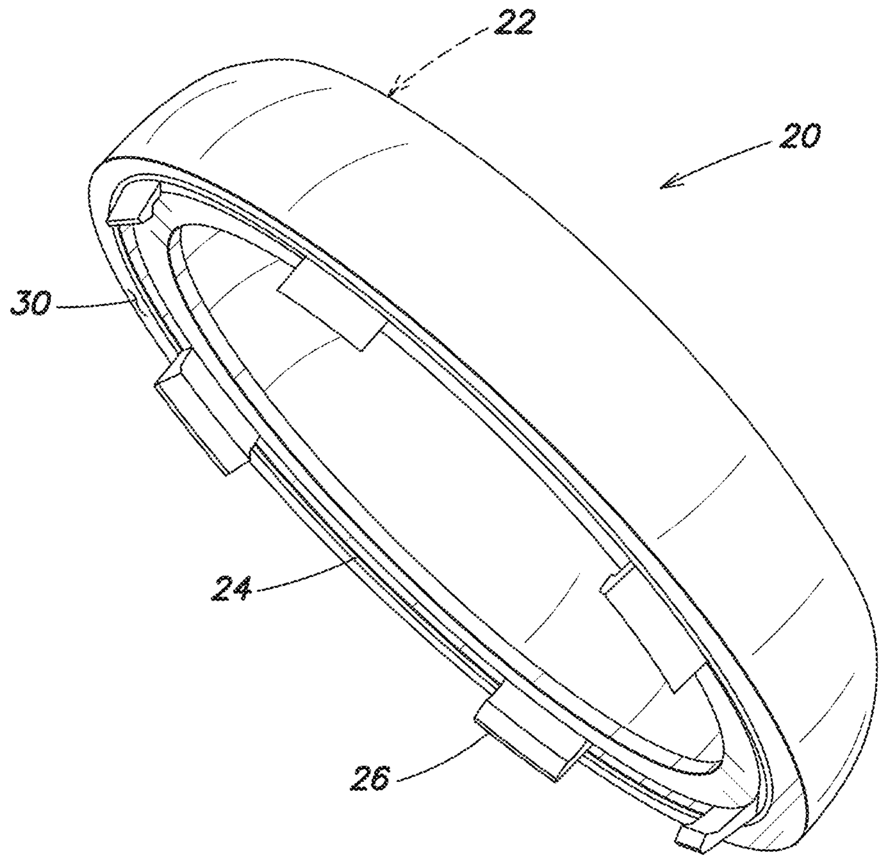
FIG. 3A is an isometric view of an implementation of a headphone earcushion.
Figure 3B:
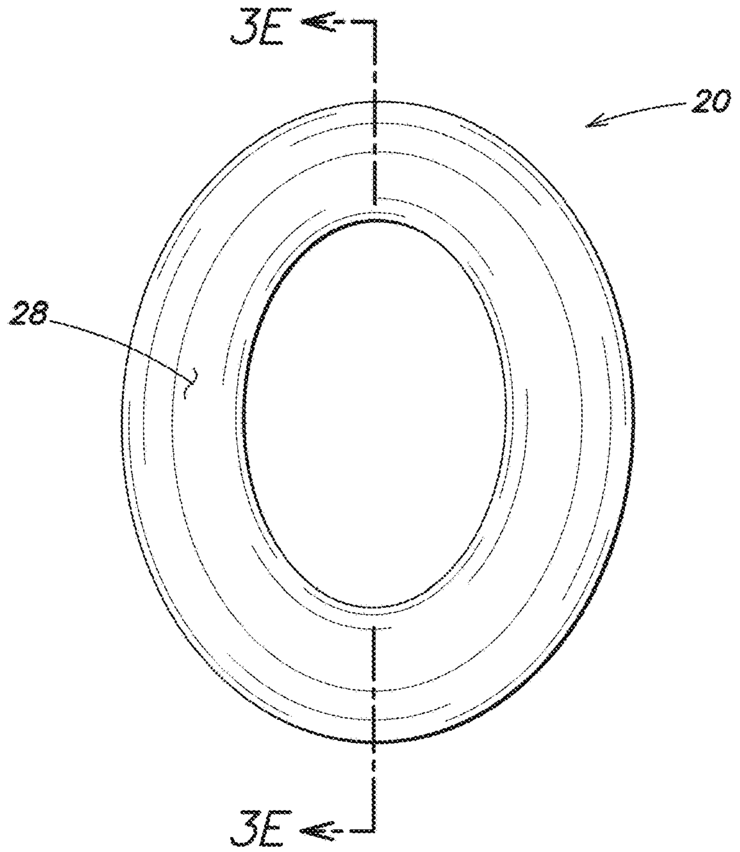
FIG. 3B is a plan view from the top of the headphone earcushion of FIG. 3A.
Figure 3C:
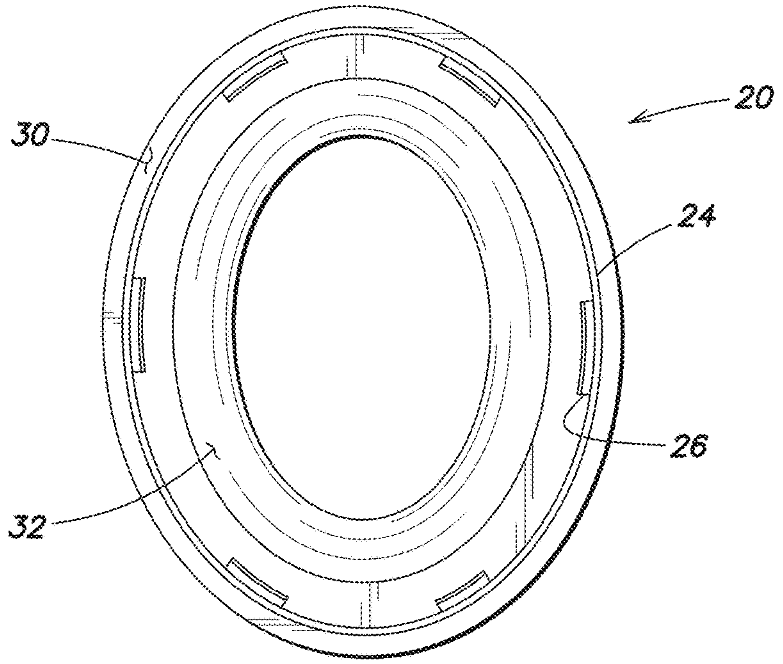
FIG. 3C is a plan view from the bottom of the headphone earcushion of FIG. 3A.
Figure 3D:
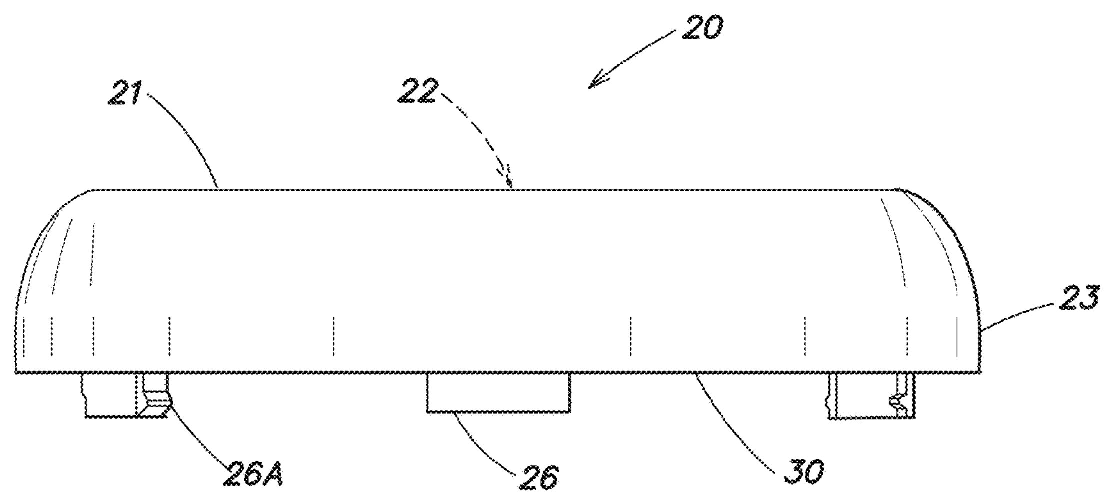
FIG. 3D is an elevational view of the headphone earcushion of FIG. 3A.
Figure 3E:
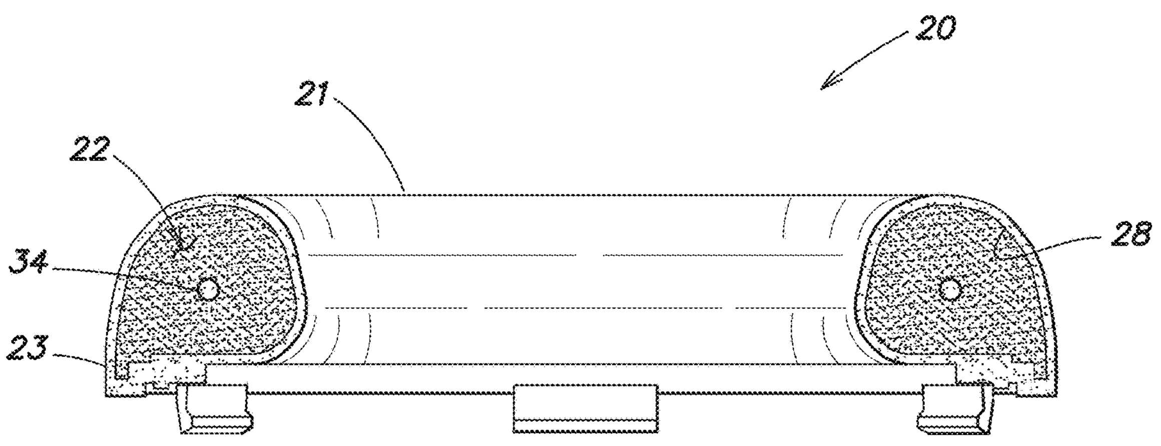
FIG. 3E is a cross-sectional view of the headphone earcushion of FIG. 3A along line 3E of FIG. 3B.

One implementation of an earcushion 20 is illustrated in isometric view in FIG. 3A, in a plan view from the top (the user contacting side) in FIG. 3B, in a plan view from the bottom (the headphone earcup contacting side) in FIG. 3C, in an elevational view in FIG. 3D, and in a cross-sectional view in FIG. 3E. The earcushion 20 may be substantially oval in shape and may be sized to either rest against or surround a user's ear 18.

Figure 4A:
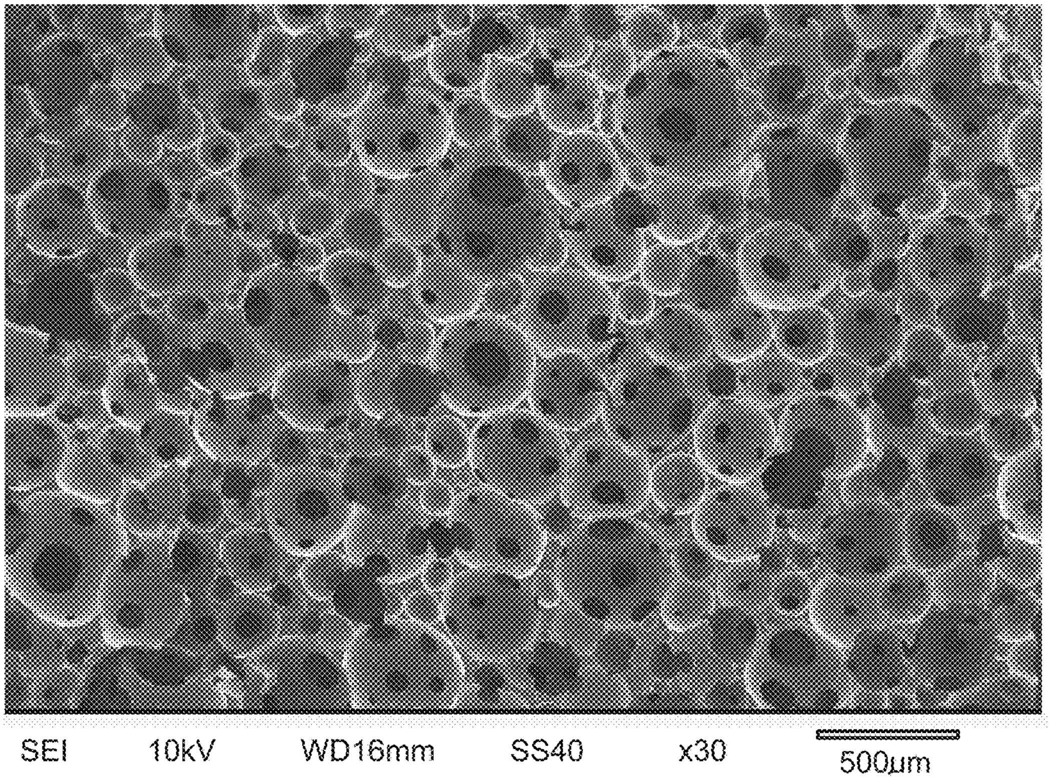
FIG. 4A illustrates cells of foam in the bulk of the body of examples of a headphone earcushion.
Figure 4B:
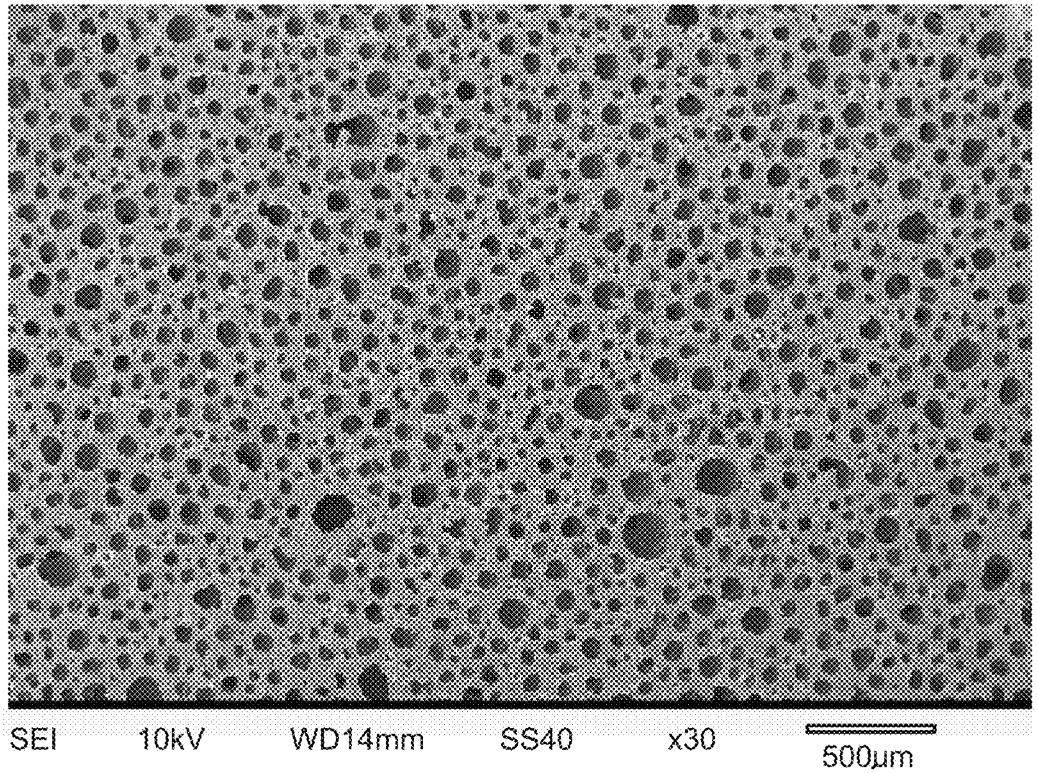
FIG. 4B illustrates cells of foam in a surface of the body of examples of a headphone earcushion.

The earcushion 20 includes a foam body 22 having an upper surface 21, side surfaces 23, and a lower surface 32. The foam body 22 may include or consist of a bulk, or inner portion, and an outer surface. Both may include or consist of a polyurethane foam and/or another type of compliant material. The material of the bulk of the foam body 22 may be a partially reticulated polymer foam having cell sizes within the bulk of the foam body 22 with diameters of between about 100 μm and about 750 μm, for example, as illustrated in FIG. 4A. The cell size at the outer surface of the foam body 22 may be smaller than that in the bulk of the foam body 22, for example, with diameters of between about 25 μm and about 100 μm, as illustrated in FIG. 4B. When uncovered by another material, the outer surface of the foam body 22 may be at least partially acoustically transparent to allow sound waves to pass through the outer surface and into the bulk of the foam body 22. The foam body 22 may allow air to flow through at a rate of about 10 $cm^3/cm^3$·second or less and may have an acoustic dampening peak at between about 1 kHz and about 2.5 kHz.

The upper surface 21 and side surfaces 23 of the foam body 22 may be covered by a substantially or wholly non-porous material 28 that reduces the tendency of external noise from entering into the foam body 22 through the upper surface 21 and side surfaces 23 of the foam body 22 and travelling to the ear of a user wearing a headphone 10 fitted with the earcushion 20. In some implementations, the substantially or wholly non-porous material 28 may be an acrylic paint film with a thickness of, for example, about 1 μm. The acrylic paint film may be more durable than materials such as polyurethane leather (pleather) used in some previous examples of earcushions and may thus have an extended life and may not shed particulate matter as some pleather materials do. The color of the acrylic paint film may be selected as desired by a manufacturer. The upper surface 21 and side surfaces 23 of the foam body 22 may be substantially smooth and include no pleats, folds, or creases. In other implementations, the upper surface 21 and/or side surfaces 23 of the foam body 22 may be molded to include a surface pattern resembling, for example, natural leather.

Figure 5:
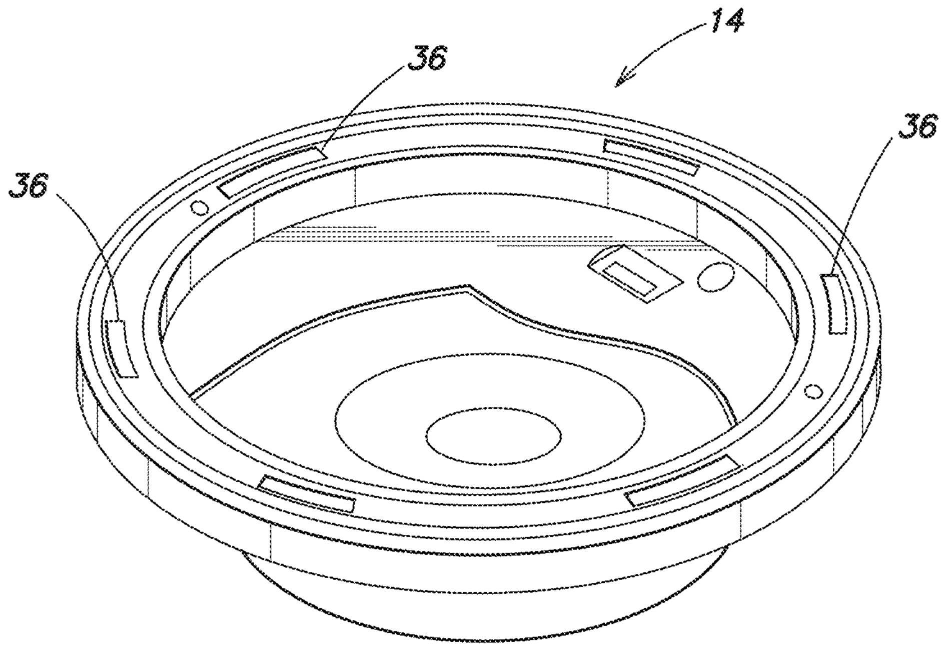
FIG. 5 illustrates an example of an earphone earcup configured to retain the headphone earcushion of FIG. 3A.

As shown in FIG. 3A, the earcushion 20 includes a snap ring 24 at least partially embedded in the foam body 22 proximate the lower surface 32 of the foam body 22. The snap ring 24 includes one or more prongs 26 extending downward from the lower surface of the snap ring 24. Six prongs 26 are illustrated in the snap ring 24 of earcushion 20 although other examples may include fewer or greater numbers of prongs 26. The lower ends of the prongs 26 opposite from the ends of the prongs 26 connected to the snap ring 24 may include hook-like structures 26A (see FIG. 3D). The prongs 26 and their hook-like structures 26A are used to retain the prongs 26, and by extension, the entire earcushion 20 in an earcup 14 of a headphone 10 having complimentary recesses 36, as illustrated in the example shown in FIG. 5. In some examples, the snap ring may be insert molded with the foam body 22 of the earcushion 20.

The snap ring 24 and prongs 26 may be formed of a material with a greater rigidity than that of the material of the body 22 of the earcushion 20. The snap ring 24 and prongs 26 may include or comprise a substantially rigid polymer, for example, polycarbonate, acrylonitrile-butadiene-styrene (ABS), acrylic glass, or poly(methyl methacrylate).

A stepped portion 30 may extend from the rear surface 32 of the body 22 of the earcushion 20 and onto an external periphery of a rear surface of the snap ring 24. The stepped portion 30 may facilitate retention of the snap ring 24 in the body 22 of the earcushion 20, thereby providing an improved seal.

At least a portion of the rear surface 32 of the body 22 of the earcushion 20 inside an inner periphery of the snap ring 24 (see FIG. 3C) may be free of the substantially or wholly non-porous material 28, thus exposing the pores on the rear surface 32 of the body 22 of the earcushion 20. The rear surface 32 of the body 22 of the earcushion 20 may thus be at least partially acoustically transparent and may allow acoustic energy to pass through the rear surface 32 of the body 22 of the earcushion 20 and into the bulk of the body 22 of the earcushion 20. The earcushion 20 may thus absorb undesirable acoustic energy present in a volume defined between the earcup 14 of a headphone 10 and the head or ear of a user, for example, sound rendered by an acoustic driver of the headphone and reflected from the ear or head of the user, or any other reverberant acoustic energy present within the earcup plenum. Absorption of such acoustic energy may increase the quality of audio perceived by a user wearing a headphone 10 fitted with the earcushion 20.

As illustrated in FIG. 3E, an acoustic dampener 34 may be embedded within the body 22 of the earcushion 20. The acoustic dampener 34 may include or consist of a material having a density greater than a density of the partially reticulated polymeric foam forming the body 22 of the earcushion 20. The material of the acoustic dampener 34 may include, for example, silicone or another polymeric material having a density greater than a density of the partially reticulated polymeric foam forming the body 22 of the earcushion 20. The acoustic dampener 34 may be a ring or a rope having a substantially oval or circular shape. The acoustic dampener 34 may increase the effective density of the body 22 of the earcushion 20 to reduce the amount of acoustic noise from outside the earcushion 20 that passes through the earcushion 20 to the ear of the user as compared to a similar earcushion 20 without the acoustic dampener 34.

Figure 6A:
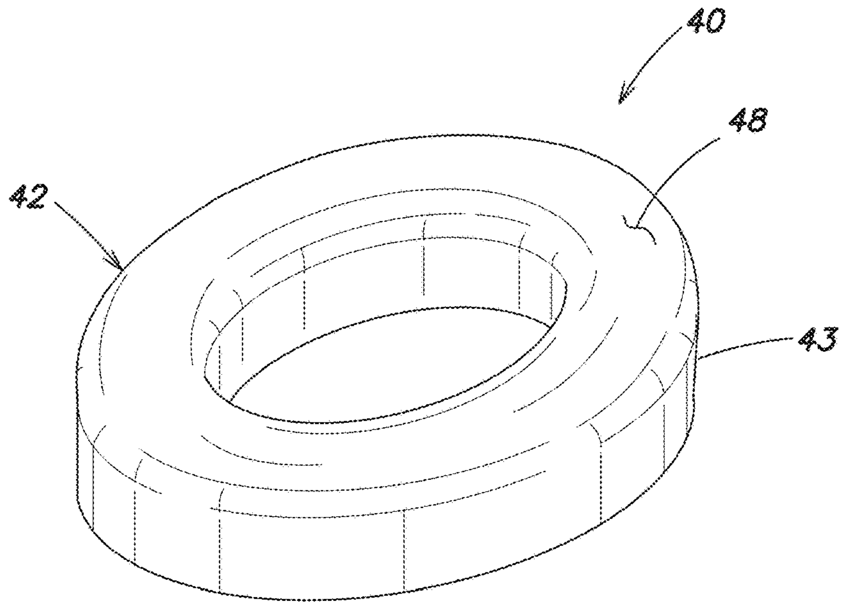
FIG. 6A is an isometric view of another implementation of a headphone earcushion.
Figure 6B:
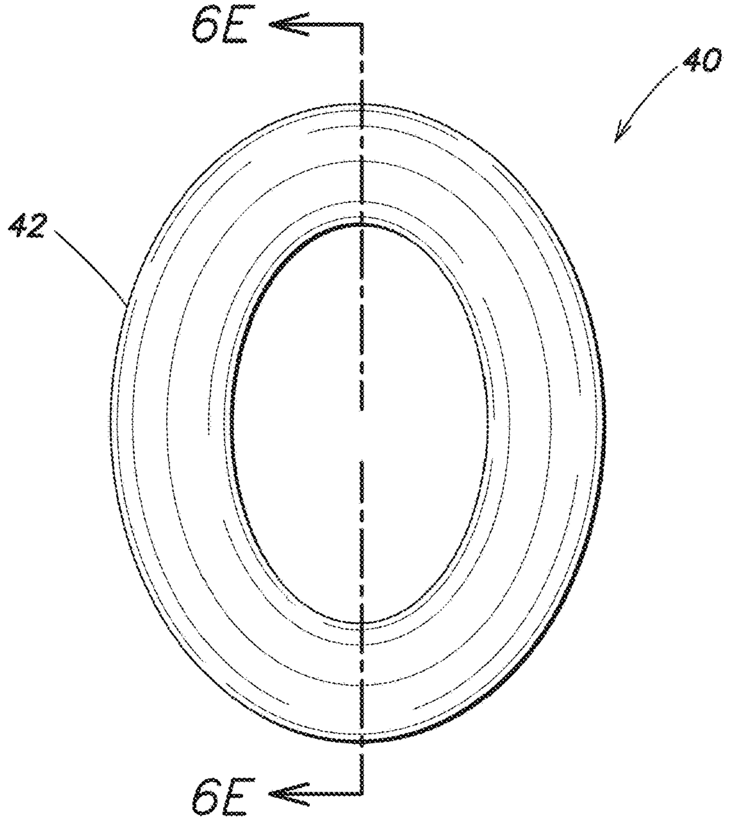
FIG. 6B is a plan view from the top of the headphone earcushion of FIG. 6A.
Figure 6C:
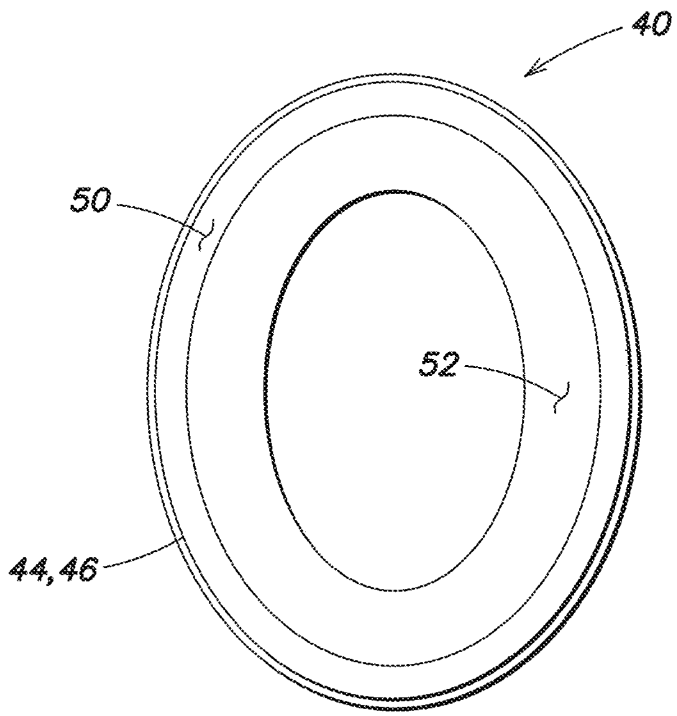
FIG. 6C is a plan view from the bottom of the headphone earcushion of FIG. 6A.
Figure 6D:
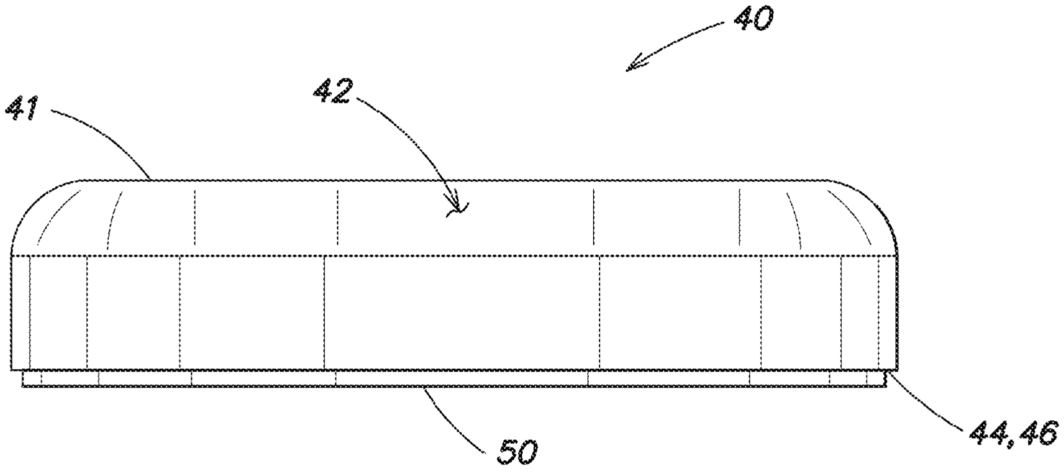
FIG. 6D is an elevational view of the headphone earcushion of FIG. 6A.
Figure 6E:
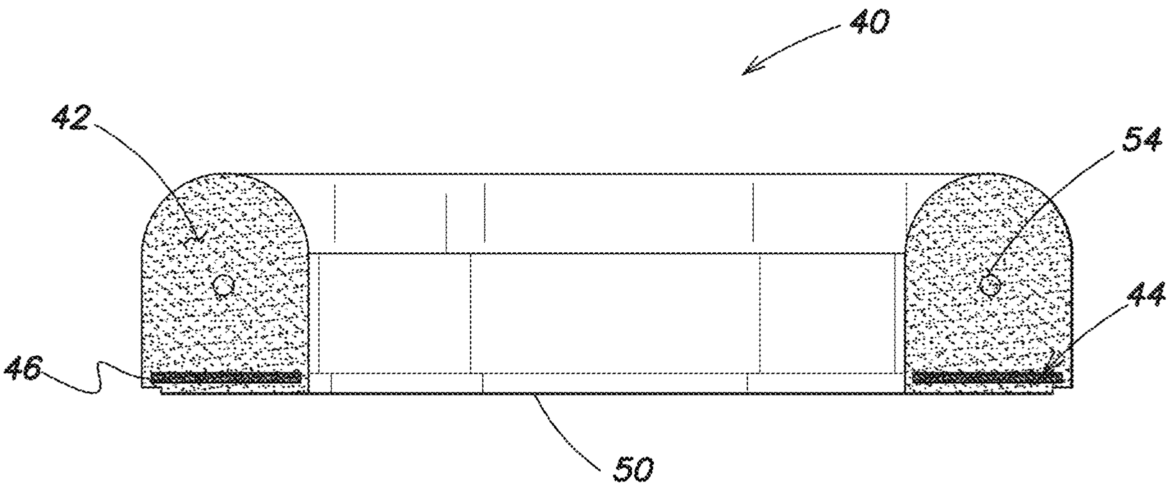
FIG. 6E is a cross-sectional view of the headphone earcushion of FIG. 6A along line 6E of FIG. 6B.

Another implementation of an earcushion 40 is illustrated in isometric view in FIG. 6A, in a plan view from the top (the user contacting side) in FIG. 6B, in a plan view from the bottom (the headphone earcup contacting side) in FIG. 6C, in an elevational view in FIG. 6D, and in a cross-sectional view in FIG. 6E. The earcushion 40 may be substantially oval in shape and may be sized to either rest against or surround a user's ear 18.

The earcushion 40 includes a foam body 42 having an upper surface 41, side surfaces 43, and a lower surface 52. The foam body 42 may include or consist of a bulk, or inner portion, and an outer surface. Both may include or consist of a polyurethane foam and/or another type of compliant material. The material of the bulk of the foam body 42 may be a partially reticulated polymer foam having cell sizes within the bulk of the foam body 42 with diameters of between about 100 μm and about 750 μm, for example, as illustrated in FIG. 4A. The cell size at the outer surface of the foam body 42 may be smaller than that in the bulk of the foam body 42, for example, with diameters of between about 25 μm and about 100 μm, as illustrated in FIG. 4B. When uncovered by another material, the outer surface of the foam body 42 may be at least partially acoustically transparent to allow sound waves to pass through the outer surface and into the bulk of the foam body 42. The foam body 42 may allow air to flow through at a rate of about 10 $cm^3/cm^3$·second or less and may have an acoustic dampening peak at between about 1 kHz and about 2.5 kHz.

The upper surface 41 and side surfaces 43 of the foam body 42 may be covered by a substantially or wholly non-porous material 48 that reduces the tendency of external noise from entering into the foam body 42 through the upper surface 41 and side surfaces of the foam body 42 and travelling to the ear of a user wearing a headphone 10 fitted with the earcushion 40. In some implementations, the substantially or wholly non-porous material 48 may be an acrylic paint film with a thickness of, for example, about 1 μm. The color of the acrylic paint film may be selected as desired by a manufacturer. The acrylic paint film may be more durable than materials such as pleather used in some previous examples of earcushions and may thus have an extended life and may not shed particulate matter as some pleather materials do. The upper surface 41 and side surfaces 43 of the foam body 42 may be substantially smooth and include no pleats, folds, or creases. In other implementations, the upper surface 41 and/or side surfaces 43 of the foam body 42 may be molded to include a surface pattern resembling, for example, natural leather.

Figure 7:
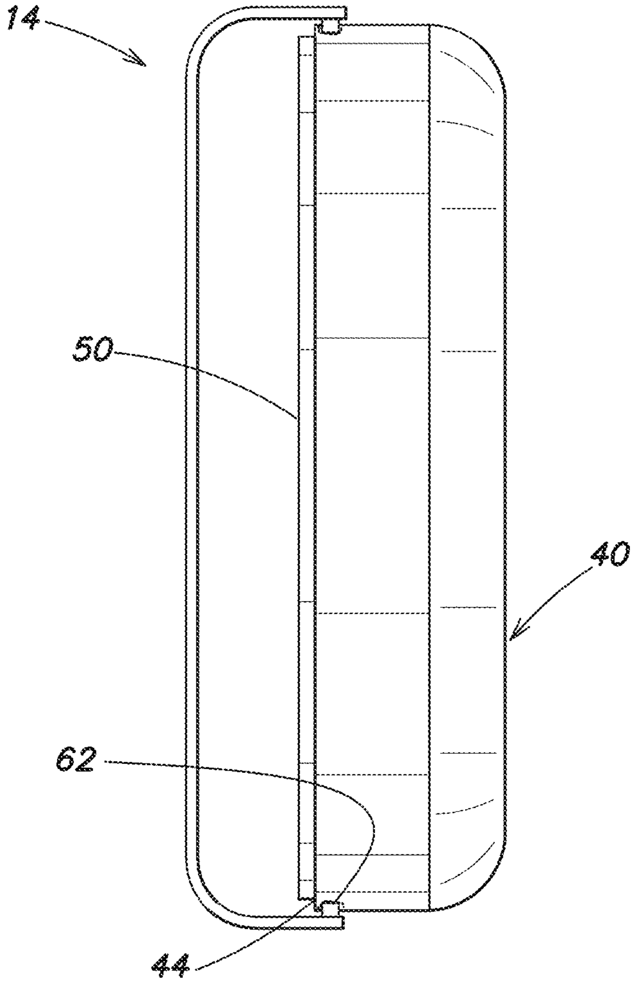
FIG. 7 illustrates an example of an earphone earcup retaining the headphone earcushion of FIG. 6A.

The earcushion 40 includes a snap ring 44 at least partially embedded in the foam body 42 proximate the lower surface 52 of the foam body 42. An outermost periphery of a front surface of the snap ring 44 may be substantially coextensive with an outer periphery of the foam body 42 of the earcushion 40. Front and rear surfaces of the snap ring 44 may be substantially planar. In other examples, the snap ring 44 may have a T-shaped cross-section for enhanced mechanical strength. The outer periphery of the snap ring 44 is configured to engage with tabs or detents 62 in an inner surface of an earcup 14 of a headphone 10 (see FIG. 7) to retain the earcushion 40 in the earcup 14.

The snap ring 44 may be formed of a material with a greater rigidity than that of the material of the body 42 of the earcushion 40. The snap ring 44 may include or comprise a substantially rigid polymer, for example, polycarbonate, acrylonitrile-butadiene-styrene (ABS), acrylic glass, or poly (methyl methacrylate).

A stepped portion 50 may extend from the rear surface 52 of the body 42 of the earcushion 40 and onto an internal periphery of a rear surface of the snap ring 44. The stepped portion 50 may facilitate connection of the snap ring 44 and the body 42 of the earcushion 40, thereby providing an improved seal. An outer peripheral portion 46 of the rear surface of the snap ring 44 may extend outwardly from beneath the stepped portion 50 of the body 42 of the earcushion 40. The outer peripheral portion 46 of the rear surface of the snap ring 44 may include exposed material of the snap ring 44 or may be covered by a thin layer, for example, about 10 μm of the material of the body 42 of the earcushion 40.

Figure 6F:
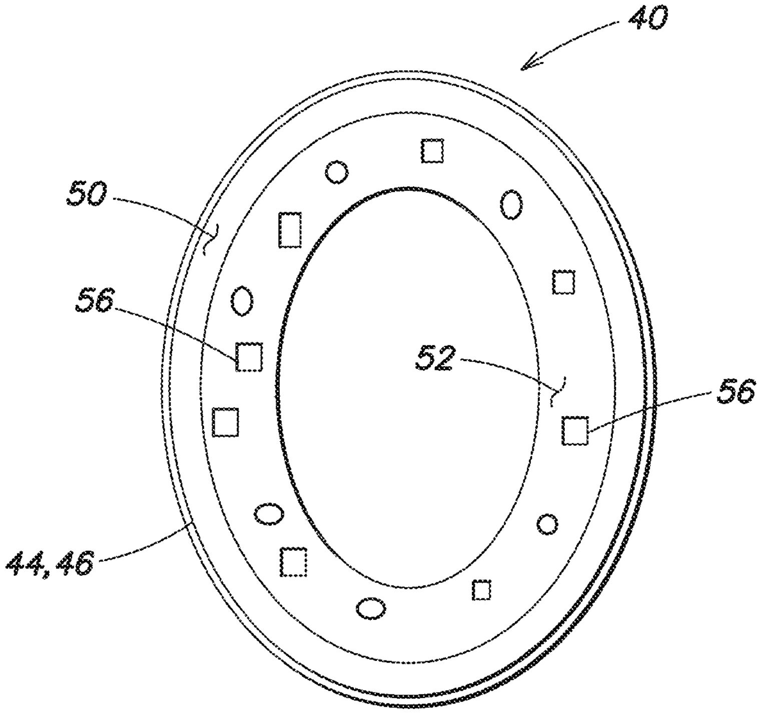
FIG. 6F is an example of the headphone earcushion of FIG. 6A including cavities defined in a rear surface.

At least a portion of the rear surface 52 of the body 42 of the earcushion 40 inside an inner periphery of the stepped portion 50 (see FIG. 6C) may be free of the substantially or wholly non-porous material 48, thus exposing the pores on the rear surface 52 of the body 42 of the earcushion 40. The rear surface 52 of the body 42 of the earcushion 40 may thus be at least partially acoustically transparent and may allow acoustic energy to pass through the rear surface 52 of the body 42 of the earcushion 40 and into the bulk of the body 42 of the earcushion 40. The earcushion 40 may thus absorb acoustic energy generated in a volume defined between the earcup 14 of a headphone 10 and the head or ear of a user, for example, sound rendered by an acoustic driver of the headphone 10 and reflected from the ear or head of the user, or any other reverberant acoustic energy present within the earcup plenum. Absorption of such acoustic energy may increase the quality of audio perceived by a user wearing a headphone 10 fitted with the earcushion 40. In some examples, as illustrated in FIG. 6F, the rear surface 52 of the body 42 of the earcushion 40 may include one or more cavities or depressions 56 extending from the rear surface 52 of the body 42 into the bulk of the body 42. The one or more cavities or depressions 56 may be circular, oval, square, rectangular, or randomly shaped. The one or more cavities or depressions 56 may increase an amount of acoustic energy that may be absorbed through the rear surface 52 of the body 42 of the earcushion and may also serve to somewhat decouple the external side wall of the earcushion from the internal sidewall of the earcushion thus reducing direct mechanical transfer of forces applied at the external sidewall to the internal sidewall 40 as compared to a similar earcushion 40 lacking the one or more cavities or depressions 56. Similar cavities or depressions 56 may be defined in the earcushion 20.

As illustrated in FIG. 6E, an acoustic dampener 54 may be embedded within the body 42 of the earcushion 40. The acoustic dampener 54 may be embedded at a substantially central location in the body 42 of the earcushion 40 as illustrated, although in alternate embodiments an acoustic dampener 54 may alternatively or additionally be located proximate upper, lower, inner, or outer surfaces of the body 42 of the earcushion 40 or proximate or in contact with the snap ring 44. The acoustic dampener 54 may include or consist of a material having a density greater than a density of the partially reticulated polymeric foam forming the body 42 of the earcushion 40. The material of the acoustic dampener 54 may include, for example, silicone, metals, ceramics or other materials having a density greater than a density of the partially reticulated polymeric foam forming the body 42 of the earcushion 40. The acoustic dampener 54 may be a ring or a rope having a substantially oval or circular shape. The acoustic dampener 54 may increase the effective density of the body 42 of the earcushion 40 to substantially attenuate the acoustic signal from outside the earcushion 40 that passes through the earcushion 40 to the ear of the user as compared to a similar earcushion 40 without the acoustic dampener 54.

Figure 6G:
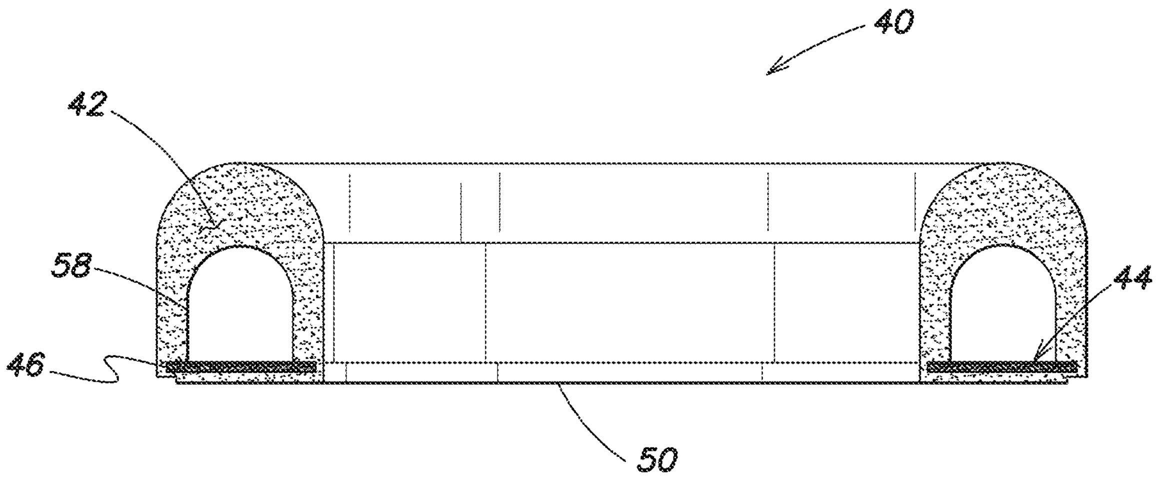
FIG. 6G is an example of the headphone earcushion of FIG. 6A including a hollowed-out portion.
Figure 6H:
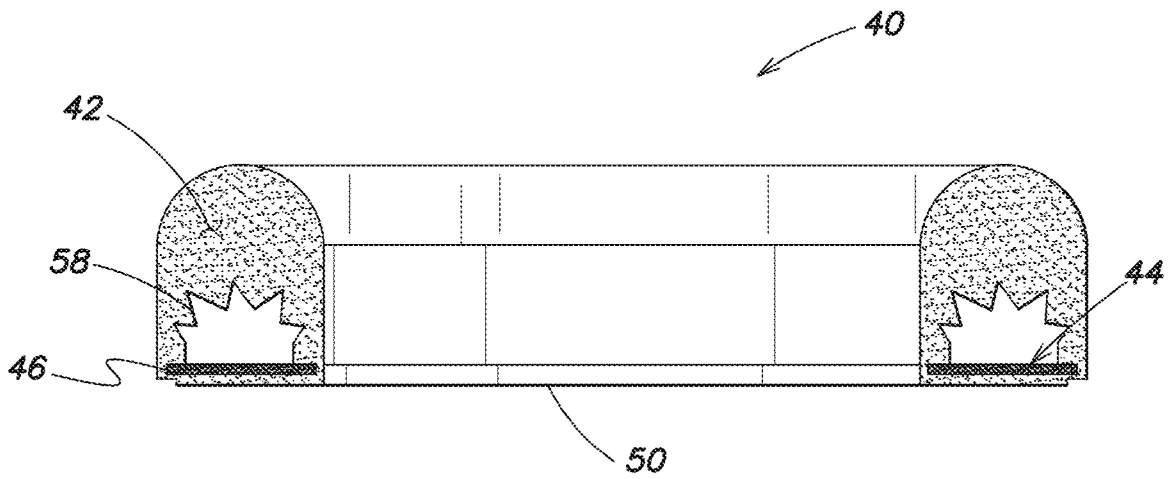
FIG. 6H is another example of the headphone earcushion of FIG. 6A including a hollowed-out portion.

In further implementations, the body 42 of the earcushion 40 may include a hollowed-out portion or molded cavity 58, as illustrated in FIG. 6G. The hollowed-out portion or molded cavity 58 may render the body 42 of the earcushion 40 substantially U-shaped. The hollowed-out portion or molded cavity 58 may increase the pliability of the earcushion 40 as compared to a similar earcushion 40 without the hollowed-out portion or molded cavity 58, rendering the earcushion 40 more comfortable for a user to wear. Such a hollowed-out portion or molded cavity may also be present in alternate examples of the earcushion 20. The hollowed-out portion or molded cavity may be formed with different shapes, for example, a star-like shape or even a random shape, for example, as illustrated in FIG. 6H. These random shapes may be designed to further enhance the listening experience of the user.

Having thus described several aspects of at least one implementation, it is to be appreciated various alterations, modifications, and improvements will readily occur to those skilled in the art. Such alterations, modifications, and improvements are intended to be part of this disclosure, and are intended to be within the spirit and scope of the disclosure. The acts of methods disclosed herein may be performed in alternate orders than illustrated, and one or more acts may be omitted, substituted, or added. One or more features of any one example disclosed herein may be combined with or substituted for one or more features of any other example disclosed. Accordingly, the foregoing description and drawings are by way of example only.

The phraseology and terminology used herein is for the purpose of description and should not be regarded as limiting. As used herein, the term "plurality" refers to two or more items or components. As used herein, dimensions which are described as being "substantially similar" should be considered to be within about 25% of one another. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. An earphone cushion comprising:

a body formed of a partially reticulated polymeric foam and including an upper surface configured to engage or surround an ear of a user, side surfaces, and a lower surface;

a snap ring at least partially embedded in the foam body proximate the lower surface and including a periphery configured to engage one or more retention elements of an earcup of a headphone; and a non-porous film disposed on the upper and side surfaces of the body.

2. The earphone cushion of claim 1, wherein the lower surface of the body is free of the non-porous film.

3. The earphone cushion of claim 2, wherein the lower surface of the body is substantially acoustically transparent.

4. The earphone cushion of claim 1, wherein the body includes a stepped portion extending from the lower surface of the body and onto an internal periphery of a rear surface of the snap ring.

5. The earphone cushion of claim 4, wherein an outer peripheral portion of the rear surface of the snap ring extends outwardly from beneath the stepped portion of the body.

6. The earphone cushion of claim 1, wherein an outer peripheral portion of the rear surface of the snap ring includes exposed material of the snap ring.

7. The earphone cushion of claim 1, wherein an outermost periphery of the snap ring is coextensive with an outer periphery of the body.

8. The earphone cushion of claim 1, wherein front and rear surfaces of the snap ring are substantially planar.

9. The earphone cushion of claim 1, wherein the snap ring has a rigidity greater than a rigidity of the partially reticulated polymeric foam.

10. The earphone cushion of claim 1, wherein an outer surface of the body extending forward from the snap ring is free of creases and folded segments.

11. The earphone cushion of claim 1, wherein the body includes a hollowed-out portion defined within the body above the snap ring.

12. The earphone cushion of claim 1, further comprising an acoustic dampener disposed within the body.

13. The earphone cushion of claim 12, wherein the acoustic dampener includes a material having a density greater than a density of the partially reticulated polymeric foam.

14. The earphone cushion of claim 13, wherein the acoustic dampener is one of ring-shaped or oval-shaped.

15. The earphone cushion of claim 1, wherein an inner portion of the lower surface of the body is substantially planar.

16. The earphone cushion of claim 1, wherein an inner portion of the lower surface of the body includes a plurality of cavities extending from the lower surface into a bulk of the body.

17. The earphone cushion of claim 1, wherein the partially reticulated polymeric foam has a cell size of between about 100 μm and about 750 μm.

18. The earphone cushion of claim 1, wherein the non-porous film includes acrylic paint.

19. The earphone cushion of claim 1, further comprising a snap ring at least partially embedded in the foam body proximate the lower surface and including one or more rearwardly extending prongs configured to engage with one or more respective receptacles in an earcup of a headphone.

20. A headset comprising:

an earcup having a front opening configured to be adjacent to an ear of a user when worn by the user; and an earphone cushion sized to secure to the front opening of the earcup, the earphone cushion including:

a body formed of a partially reticulated polymeric foam and including an upper surface configured to engage or surround the ear of the user, side surfaces, and a lower surface;

an acoustic dampener disposed within the body; and a non-porous film disposed on the upper and side surfaces of the body.

21. The headset of claim 20, further comprising a snap ring at least partially embedded in the foam body proximate the lower surface including a periphery configured to engage one or more retention elements in the earcup.

22. The headset of claim 21, wherein the one or more retention elements in the earcup include one or more detents extending inwardly from an inner wall of the earcup.

23. The headset of claim 22, wherein the snap ring is configured to engage rear surfaces of the one or more detents to secure the earphone cushion to the front opening of the earcup.

24. The headset of claim 21, wherein the body of the earphone cushion includes a stepped portion extending from the lower surface of the body, onto an internal periphery of a rear surface of the snap ring, and into an interior portion of the earcup.

25. The headset of claim 20, further comprising a snap ring at least partially embedded in the foam body proximate the lower surface and including one or more rearwardly extending prongs configured to engage with one or more respective retention elements in the earcup.

26. The headset of claim 25, wherein the one or more retention elements in the earcup include one or more slots configured to receive the one or more rearwardly extending prongs.

* * * * *